US00PP09420P

United States Patent [19]

Olesen et al.

[11] Patent Number: Plant 9,420

[45] Date of Patent: Jan. 9, 1996

[54] MINIATURE ROSE PLANT NAMED 'POULXAS'

[75] Inventors: Mogens N. Olesen; Pernille Olesen, both of Fredensborg, Denmark

[73] Assignee: Weeks Wholesale Rose Grower, Inc., Upland, Calif.

[21] Appl. No.: 367,811

[22] Filed: Jan. 3, 1995

[51] Int. Cl.[6] ..... A01H 5/00

[52] U.S. Cl. ..... Plt./10.1

[58] Field of Search ..... Plt./8.2, 10.1

*Primary Examiner*—Howard J. Locker

*Attorney, Agent, or Firm*—Christie, Parker & Hale

[57] ABSTRACT

A new variety of miniature rose suitable for garden decoration, having flowers of apricot orange coloration.

1 Drawing Sheet

BACKGROUND OF THE INVENTION

This invention relates to a new and distinct variety of miniature rose. The varietal denomination of the new variety is 'Poulxas'. The plant is an upright miniature rose bush cultivated for outdoor garden decoration. It has as its seed parent an unnamed seedling, and as its pollen parent 'Poultex' (U.S. Plant Pat. No. 6,261).

SUMMARY OF THE INVENTION

Among the features which distinguish the new variety from other presently available and known commercial rose cultivars are the following combination of characteristics: few thorns on stems, its lasting apricot orange color, its full petaled flowers of an old garden rose form and its bright green foliage. 'Poulxas' may be asexually propagated by cuttings, budding, and grafting.

Asexual reproduction of the new variety as performed by budding in Kern County and Upland, Calif., shows that the foregoing and other distinguishing characteristics come true to form and are established and transmitted through succeeding propagations.

COMPARISON WITH PARENT VARIETIES

The new rose may be distinguished from its unnamed seed parent by the following combination of characteristics: whereas 'Poulxas' bears flowers of an apricot orange coloration, the seed parent bears flowers of an orange-red coloration with a yellow reverse. The plant habit of the seed parent is rounded, compact and low, whereas the new variety has a taller, more upright plant habit.

The new variety may be distinguished from its pollen parent, 'Poultex' by the following combination of characteristics: whereas 'Poulxas' bears flowers of an apricot orange coloration, the pollen parent bears flowers of a yellow coloration. The new variety bears very full petaled flowers, whereas 'Poultex' bears flowers with significantly fewer petals.

BRIEF DESCRIPTION OF THE ILLUSTRATION

The accompanying photograph illustrates the plant in color and shows the flowering thereof from bud to full bloom depicted in color as nearly correct as it is possible to make in a color illustration of the character. Throughout this specification, color values are based upon The Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of September. Phenotypic expression may vary with environmental, cultural and climatic conditions, as well as differences in conditions of light and soil.

FLOWER

The new variety bears its flowers sometimes singly, but mostly three or more per stem. Flowers are borne in irregular, rounded clusters on average strong, short-to-medium length stems (about 10 to about 19 cm) for the class. Outdoors the plant blooms very abundantly and nearly continuously during the growing season. The flowers have a slight spicy fragrance.

BUD

The peduncle is of medium to long length for the class (about 3.5 to about 5 cm), of average caliper, and usually erect. It is mostly smooth with some stipitate glands. Peduncle color is between 144A and 138B.

Before the calyx breaks, the bud is of medium size for the class (about 0.9 to about 1.3 cm in diameter at the widest point), medium in length (about 1.5 to about 2 cm), and pointed to ovoid in shape. The surface of the bud bears numerous hairs and some stipitate glands, usually with slender foliaceous parts extending beyond the tip of the bud equal to ¼ or more of its length. Bud color is between 144A and 138B.

The inner surface of the sepals is covered with fine wooly tomentum; sepal margins are lined with few stipitate glands and some hairs.

As the petals open, the bud is medium sized for the class (about 1 to about 1.4 cm in diameter at the widest point), medium in length (about 1.5 to about 2 cm), and pointed to ovoid in form. The color of the under and upper surfaces of the newly opened petals is between 23C and 20C. The bud opens well and is generally not prevented from opening by wet, cold, hot or dry weather.

BLOOM

When fully open, the bloom is medium to large for the class, ranging from about 3.5 to 5 cm in diameter. Petalage is very double with about 55 to 72 petals and numerour petaloids arranged regularly. When partially open, the bloom form is somewhat cupped, and the petals are loosely spiraled-to-cupped in form with petal edges slightly rolled outward. When fully open, the bloom form is very cupped and full-to-flat, and the petals are more loosely cupped-to-flat with petal edges very slightly rolled outward.

PETALS

The petals are of good substance and of medium thickness, with upper surfaces slightly shiny to satiny and under surfaces satiny. The outer petals are nearly round to broadly ovate in shape with rounded apices. The intermediate petals are more broadly obovate with rounded apices. The inner petals are very narrowly obovate to lanceolate in shape with rounded apices.

NEWLY OPENED FLOWER

The under surface of the outer, intermediate and inner petals is between 21D and 22C. The upper surface of the outer, intermediate and inner petals is between 19B and 23D.

The general tonality of the newly opened flower is between 19B and 23D.

THREE DAY OLD FLOWER

The under surface of the outer and inner petals is between 19B and 23D. The upper surface of the outer and inner petals is between 20D and 19C.

The general tonality of the three day old flower is between 20D and 19C.

The petals usually persist on the spent blooms before falling away, fading to near 19D.

In September in Upland, Calif., blooms on the bush growing outdoor generally last from four to five days. Cut roses grown outdoor and kept at normal indoor living temperatures generally last from four to five or more days.

MALE REPRODUCTIVE ORGANS

Stamens are few in number and are arranged irregularly about the pistil; a few are mixed with petaloids or tucked in the calyx. The filaments are irregular in length, many without anthers. The anthers are small to medium for the class and all open aproximately at the same time. Anther color is near 21D when immature and near 167D at maturity. Pollen is very sparse and near 20D in color.

FEMALE REPRODUCTIVE ORGANS

Pistils are very few in number (approximately 18). The styles are uneven to short in length, thin to average in caliper, and loosely bunched. Stigma and style color is near 4C. Ovaries are usually all enclosed in the calyx.

Hips have not been observed on plants of this variety grown in Upland, Calif.

FOLIAGE

The compound leaves are usually comprised of three to five leaflets and are borne in normal quantities. The leaves are medium for the class (about 5 to about 6.5 cm in length and about 3 to about 4 cm in width at the widest point), normal to heavy in texture, and slightly semi-glossy to matte in finish. The leaflets are medium in size for the class (about 1.5 to about 2.5 cm in length and about 1.2 to about 1.7 cm in width at the widest point), oval to ovate in shape with acute apices and rounded bases. Their margins are usually dentate.

The upper surface of the mature leaf is between 147A and 139A. The under surface of the mature leaf is between 138B and 191B. The upper and under surface of the young leaf is between 146B and 137C, sometimes very lightly suffused with near 183B.

The rachis is average in caliper. The upper side is grooved and very smooth with few hairs and stipitate glands. The under side of the rachis is mostly smooth with few stipitate glands and 1 to 2 very small prickles.

The stipules are medium to long in length with narrow to medium width and medium length straight points that sometimes turn out at an angle of less than 45 degrees.

The plant displays an average degree of resistance to powdery mildew and rust as compared to other commercial varieties grown under comparable conditions in Upland, Calif.

GROWTH

The plant has a miniature bushy upright medium height habit for the class (about 48 to about 60 cm in height and about 32 to about 44 cm spread at the widest point), with very full branching. It displays very vigorous growth and the canes are of good caliper for the class.

The color of the major stems is between 147B and 138B. The stems bear very few small to medium size prickles which are short to medium length for the class (about 0.3 about 0.4 cm). The prickles are almost straight angled slightly downward with a medium to long narrow base; prickle color is near 165B. The major stem bears no small prickles.

The color of the branches is between 146A and 138A. The branches bear a few small to medium size prickles which are short to medium length for the class (about 0.3 about 0.4 cm). The prickles are almost straight angled slightly downward with a medium to long narrow base; prickle color is near 161D. The branches bear no small prickles.

The color of the new shoots is between 144A and 143C sometimes very lightly suffused with near 183B. They bear a few small to medium size prickles which are short to medium length for the class (about 0.3 about 0.4 cm). The prickles are almost straight, angled slightly downward with a medium to long narrow base; prickle color is near 144C. The shoots bear no small prickles.

We claim:

1. A new and distinct variety of miniature rose plant substantially as described and illustrated herein.

* * * * *

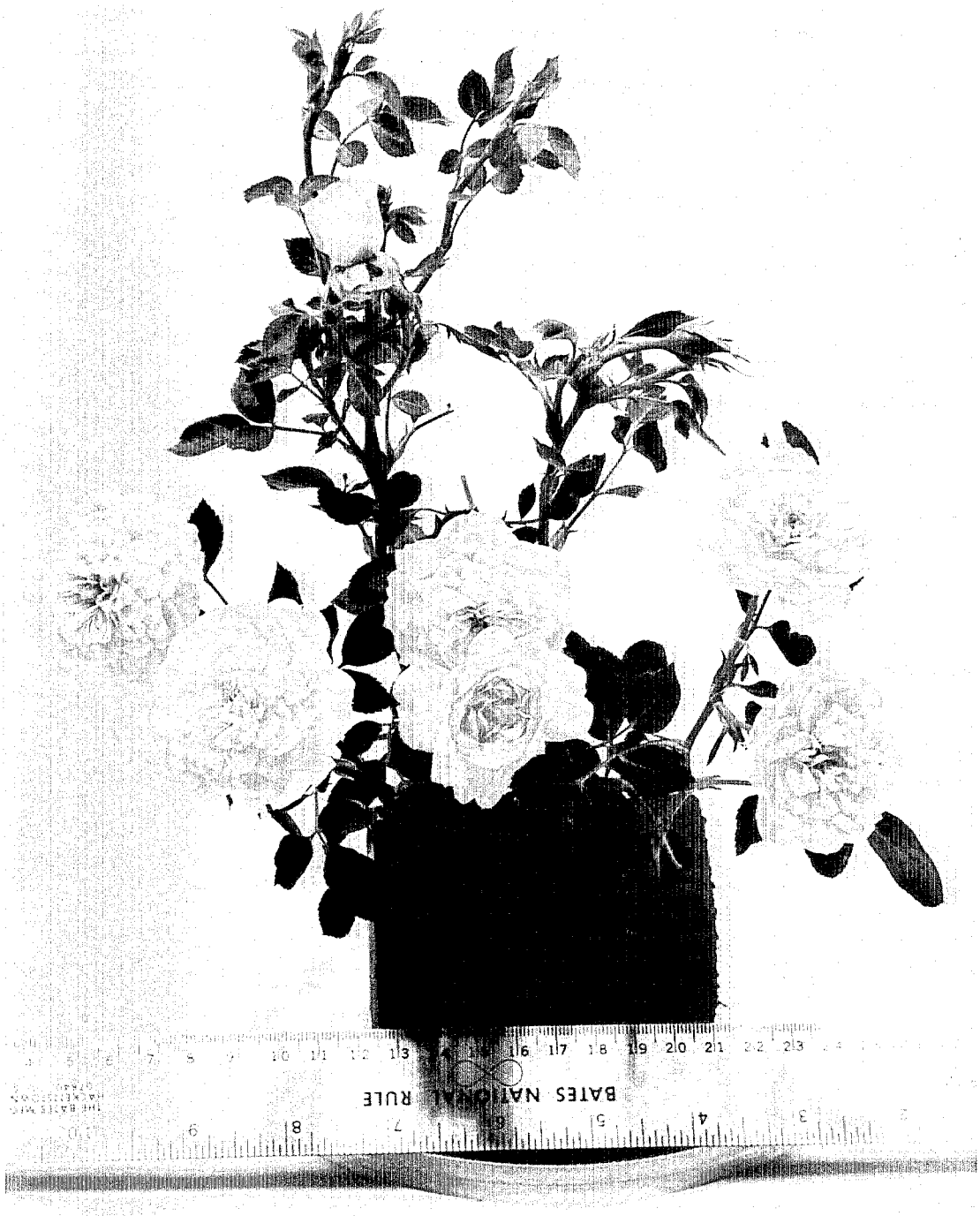
BATES NATIONAL RULE